United States Patent [19]

Inomata et al.

[11] Patent Number: 4,490,833
[45] Date of Patent: Dec. 25, 1984

[54] X-RAY PHOTOGRAPHIC INSPECTING DEVICE

[75] Inventors: Masashi Inomata; Shizuo Kon; Tsukasa Kaku; Shizuo Shinohara, all of Sapporo, Japan

[73] Assignee: Hoxan Corporation, Sapporo, Japan

[21] Appl. No.: 550,726

[22] Filed: Nov. 14, 1983

[30] Foreign Application Priority Data

Sep. 12, 1980 [JP] Japan .................. 55-126670

[51] Int. Cl.³ ............................................. G03B 41/16
[52] U.S. Cl. ........................................ 378/58; 378/197
[58] Field of Search ........................... 378/58, 59, 197

[56] References Cited

U.S. PATENT DOCUMENTS 3,430,044 2/1969 Breffaud .......................... 378/58

Primary Examiner—Craig E. Church
Attorney, Agent, or Firm—George B. Oujevolk

[57] ABSTRACT

An X-ray photographic inspecting device for inspecting a welded part such as, for example, a vertical welded part on a wall to be inspected like the wall of a metal tank, which has a body movable at the upper edge of the wall to be inspected and supported by a supporting leg on the wall to be inspected, an X-ray generator elevationally and movably hung at a guide rail vertically provided at the body, and a radiological transmitter mounted on a support provided at the X-ray generator. This entire device can be operated by a single worker or operator by an operational panel on a gondola, which drives the X-ray generator and the gondola, fixing the body to the wall with magnets or releasing the fixture of the body, urging the transmitter onto the wall to be inspected, bonding the film on the opposite side of the wall to be inspected, and carrying out the X-ray photographing of the welded part on the wall to be inspected.

1 Claim, 7 Drawing Figures

X-RAY PHOTOGRAPHIC INSPECTING DEVICE

BACKGROUND OF THE INVENTION

This invention relates to an X-ray photographic inspecting device and, more particularly, to improvements in an X-ray photographic inspecting device for inspecting the welded part of a wall to be inspected such as, for example, a large size metal gas tank wall or the like.

Generally, a large size metal gas tank a is, as shown in FIGS. 1 and 2, manufactured by welding a number of metal plates b, . . . in both longitudinal and lateral directions with each other. The weldability of the welded parts c, . . . among the metal plates is normally inspected by an X-ray photographing while manufacturing the tank.

There is presently known a conventional X-ray photographic inspection device as indicated in FIG. 3. This device has a body e movable along the upper edge d' of a wall d which is to be inspected such as the wall of a tank, an X-ray generator f hung through a rop g from one side of the surface of the wall d, and a gondola h installed at the other side of the surface of the wall d. A worker or an operator i on the gondola h adjusts the height of the X-ray generator f while pulling the rope g and thus positions the X-ray generator f at the welded part c of the metal plates b on the wall d to be inspected. Another worker or operator i' on the ground imparts a tension to the rope g so that the X-ray generator f may not laterally rock. In this state, the other worker or operator i" on a ladder j vertically suspended from the body e takes the X-ray photograph.

In the above described conventional X-ray photographic inspecting device, the X-ray generator f is manually or artificially moved elevationally upwardly or downwardly, positioned and fixed. Accordingly, this device necessitates at least three workers or operators so as to fix the X-ray photographic inspecting device to the predetermined position of the welded part on the wall to be inspected. In addition, the foregoing work is dangerous, and the positioning operation of the X-ray generator is inaccurate. Therefore, errors tend to occur in the inspection. Further, the aforementioned work is very inefficient. Thus, it takes a great deal of labor and time in the inspection of one large-sized tank.

SUMMARY OF THE INVENTION

Accordingly, a primary object of this invention is to provide an X-ray photographic inspecting device which can eliminate the aforementioned disadvantages and drawbacks of the conventional X-ray photographic inspecting device and which all the equipment can be operated by a single worker or operator on an operation panel.

Another object of this invention is to provide an X-ray photographic inspecting device which can automatically position an X-ray generator thereof.

A further object of this invention is to provide an X-ray photographic inspecting device which can accurately and rapidly position the X-ray generator at every welded part to be inspected.

Still another object of this invention is to provide an X-ray photographic inspecting device which can be operated Still another object of the invention is to provide an X-ray photographic inspecting device which can be operated safely.

According to one aspect of the invention, there is provided an X-ray photographic inspecting device which comprises a body movable at the upper edge of a wall to be unspected such as, for example, the wall of a tank or the like and supported by a supporting leg on the wall to be inspected, an X-ray generator elevationally and movably hung vertically on a guide rail provided at the body, a radiological or X-ray transmitter mounted on a support provided at the X-ray generator in such a manner that the transmitter can be urged onto the wall to be inspected, and drive means for driving the penetrameter support.

The above and other related objects and features of the invention will be apprent from a reading of the following description of the disclosure found in the accompanying drawings and the novelty thereof pointed out in the appended claims.

DESCRIPTION OF THE PREFERRED EMBODIMENTS

Figure 4:
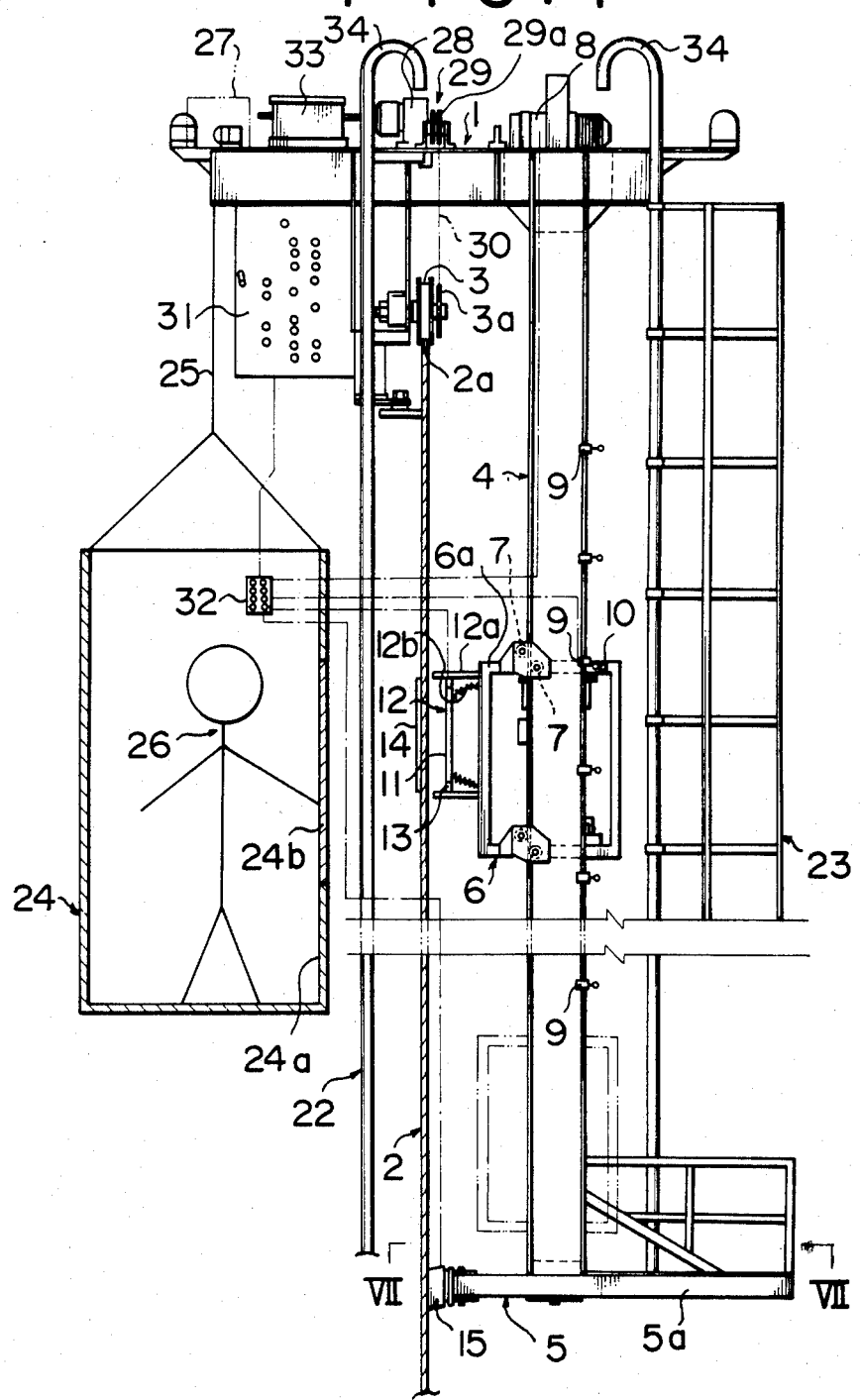
FIG. 4 is a side view showing a preferred embodiment of the X-ray photographic inspecting device for a welded part constructed according to this invention while in use.

Reference is made to the drawings, particularly to FIGS. 4 through 7 showing one preferred embodiment of the X-ray photographic inspecting device constructed according to this invention, wherein like reference numerals designate the same parts in the respective views. A body or housing 1 is assembled with suitable members made of steel or the like in a framework of rectangular shape being long in lateral direction. The body 1 includes at least two wheels 3, 3 laterally journalled at an adequate interval in a longitudinal direction and movable at the upper edge 2a of a wall 2 to be inspected such as, for example, the wall of a tank or the like as a guide. A guide rail 4 is vertically installed along one side surface of the wall 2 to be inspected. A supporting leg 5 is laterally mounted at the lower end of the rail 4 on the wall 2 to be inspected. The body 1 is supported by the supporting leg 5 on the wall 2 to be inspected as indicated in FIG. 4.

An X-ray generator 6 is elevationally and movably driven with rollers 7, 7 along the guide rail 4 and is hung from an electric chain block 8 carried on the body 1. A plurality of limit switches 9, . . . are movably adjustably mounted at a predetermined interval in a vertical direction, that is, at the length unit corresponding to the length of the vertically welded part C indicated in FIG. 2. The X-ray generator 6 is elevationally moved up or down by the chain block 8. When a sensor 10 mounted at the X-ray generator 6 makes contact with any of the limit switches 9, it senses the position to be stopped and the X-ray generator 6 will stop at the position to allow the X-ray generator 6 to coincide with the vertical welded part c on the wall 2 to be inspected.

The X-ray generator 6 also includes a radiological transmitter support 12 for moving a penetrameter 11 toward the wall 2 to be inspected at the side opposite to the surface of the wall 2 to be inspected, and a drive means for driving the penetrameter support 13.

The transmitter 11 also serves to photograph or project an identifying letter, symbol or the like on a film 14 in photographing the vertical welded part c so as to identify a part and determine whether the part c should again be photographed or not. The transmitter support 12 is supported via springs 12b interposed within a supporting frame 12a projected forwardly from the frame 6a of the X-ray generator 6. A drive means for driving the penetrameter support 12 may includes, for example a magnet, a motor-driven cylinder or the like. The drive means is electrically connected to the limit switches 9, and operates in synchronism with the stop of the X-ray generator 6 to position the transmitter 11 opposite the position on the wall 2 to be inspected.

Figure 7:
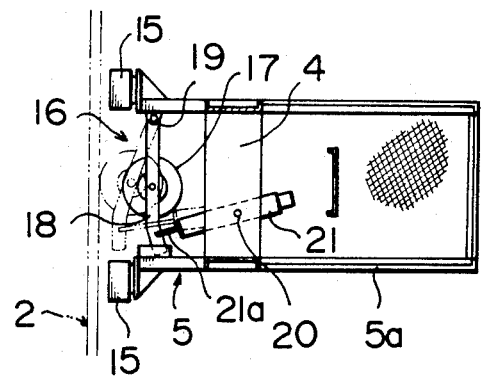
FIG. 7 is a cross sectional view of the device taken along the line VII–VII with arrows in FIG. 4.

As evident from FIG. 7, the supporting leg 5 is formed in substantially U shape in a horizontal plane. The leg 5 includes two leg frames 5a laterally fixed to the lower ends of the guide rail 4, and at least two magnets 15, 15 secured at an appropriate interval to the left and right front ends of the frame 5a. Thus, the body 1 is stably supported via two-fulcrum supports with the magnets 15, 15 onto the wall 2 to be inspected. The leg 5 also includes pushing means 16 with a wheel 17 for urging the wall 2 to be inspected and thereby separating the fixture via the magnets 15, 15 from the leg to the wall 2 to be inspected.

The pushing means 16 with the wheel 17 is formed by pivotally securing at a pivot 19 the one end of an arm 18 for journalling the wheel 17 to the one side end of the frame 5a and connecting the movable end of the arm 18 to the output shaft 21a of a cylinder 21 pivotally secured at a pivot 20 to the frame 5a.

Thus, when the cylinder 21 is driven in the state that the legs are secured by the magnets 15, 15 to the wall 2 to be inspected and the wall 2 is urged by the wheel 17 to be moved forward through the arm 18, the fixture of the leg to the wall to be inspected can be isolated as designated by two-dotted broken lines. Since the wheel 17 rolls on the surface of the wall 2 to be inspected in such isolated state, the body 1 can be smoothly moved with respect to the wall 2 to be inspected.

Referring back to FIG. 4, ladders 22 and 23 are vertically hung at both inside and outside of the wall 2 to be inspected from the body 1 and are used for inspecting the welded parts on the wall 2 and adjusting respective parts. Further, a gondola 24 is elevationally and movably driven via a wire 25 hung along the side, symmetrical with the X-ray generator 6 with respect to the wall 2 to be inspected.

The gondola 24 is formed of a lead stationary frame 24a capable of preventing the transmission of an X-ray therethrough at least on the front surface, and an openable door 24b clamped by screws to the stationary frame 24a for securing the safety of a worker or operator 26 on the gondola 24.

The gondola 24 is elevationally moved in synchronism with the elevational movement of the X-ray generator 6. The gondola 24 may be driven by the electric chain block 8 as a drive source of the X-ray generator 6 or may also be driven by using a wire winch (not shown) via a motor 27 carried on the body 1. In both cases, the gondola 24 is so set beforehand as to be elevationally driven in synchronizm with the elevational movement of the X-ray generator 6.

As shown in FIG. 4, the drive source of the body 1 includes a motor 28 carred on the body 1, and a reduction gear 29 interlocked with the motor 28 and having a sprocket 29a, another sprocket 3a fixed to the shaft of the wheel 3 for horizontally moving, and a chain 30 wound around the sprockets 39a and 3a.

An operation panel 32 connected to a control panel 31 is disposed within the gondola 24. The respective drive sources can be energized or deenergized by operating the operation panel 32 thereby fixing the body 1 via the supporting leg 5 on the wall 2 to be inspected or releasing the fixture of the body 1, moving or stopping the body 1, elevationally moving the X-ray generator 6 and the gondola 24, pushing the penetrameter, and taking photograph of the X-ray and so forth as all the operations.

Figure 5:
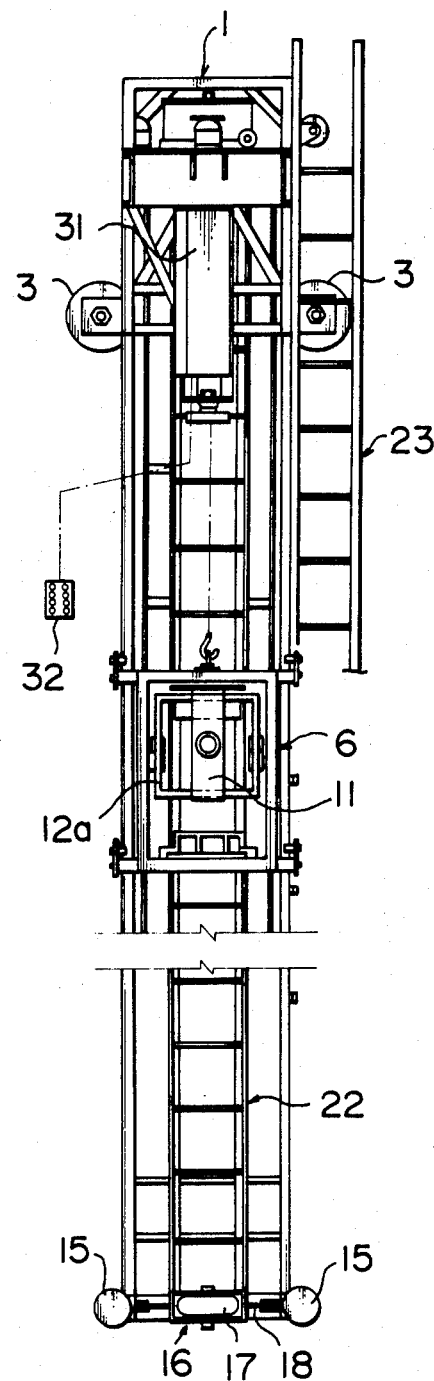
FIG. 5 is a front view of the device of the invention shown in FIG. 4.
Figure 6:
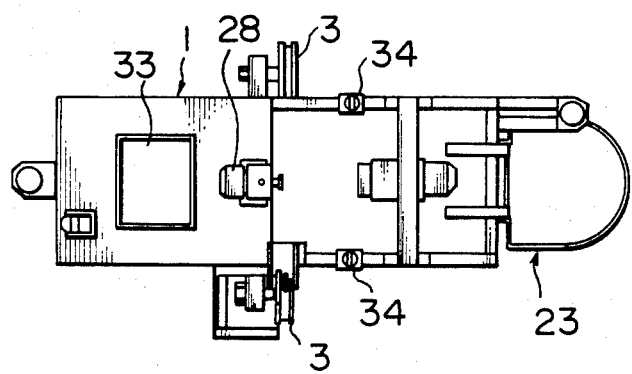
FIG. 6 is a plan view of the device of the invention shown in FIG. 4.

In FIGS. 4 through 6, reference numeral 33 designate a controller, and 34 a hanger.

Figure 1:
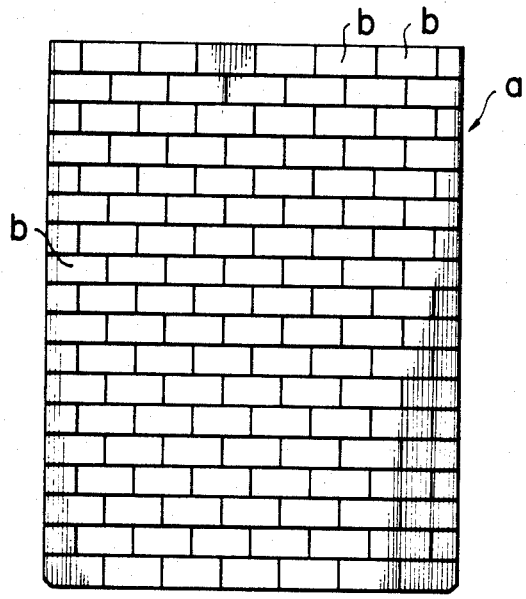
FIG. 1 is a front view showing an example of a metal tank.
Figure 2:
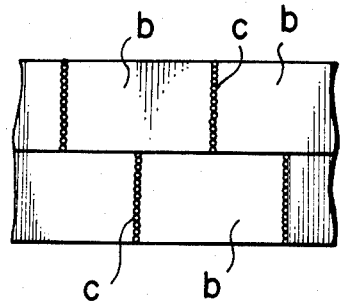
FIG. 2 is a partially enlarged front view of the tank shown in FIG. 1.
Figure 3:
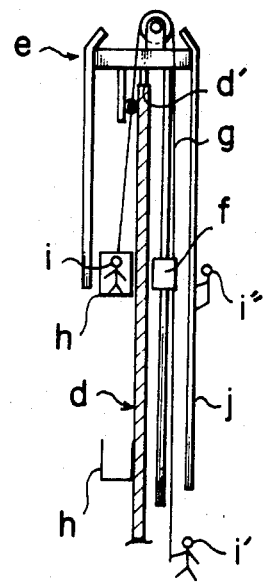
FIG. 3 is a side view showing the conventional X-ray photographic inspecting device for the welded part.

When the wall 2 to be inspected such as, for example, the wall of a metal tank indicated in FIG. 2 is taken by the X-ray photograph at the vertical welded part c with the X-ray photographic inspecting device thus constructed, a wire is first hung on the hangers 24, and is then hung up by a crane or the like, horizontally moving wheels 3 are then engaged with the upper edge 2a of the wall 2 to be inspected, and the X-ray photographic inspecting device of this invention is hung on the wall 2 to be inspected as indicated in FIG. 4.

After the X-ray photographic inspecting device of this invention is thus hung, a worker or operator 26 will ride on the gondola 24 by utilizing the ladder 22. When the worker 26 then starts the motor 28 via the operation panel 32, the horizontally moving wheels 33 are rotated to allow the body 1 to be horizontally move with the upper edge 2a of the wall 2 to be inspected as a guide. Thus, the X-ray generator 6 is moved to coincide with the vertical welded part c on the wall 2 to be inspected.

If the wheel 11 is moved or pushed forwardly by the pushing means 16 of the supporting leg 5 at this time, since the wheel 17 is rolled on the surface of the wall 2 to be inspected, the body 1 can be smoothly hozizontally moved.

After the body 1 is moved to a predetermined position, when the pushing means 16 is operated on the operation panel 32 to allow the wheel 7 to be retarded, the magnets 15, 15 operates to act on the metal wall 2 to be inspected. Accordingly, the body 1 is secured by the supporting leg 5 to the wall 2 to be inspected without lateral fluctuation.

Then, the electric chain block 8 and the motor 27 are started on the operation panel 32 to allow the X-ray generator 6 and the gondola 24 to be elevationally moved and positioned to desired vertical welded part c.

It should be noted that, since the limit switches 9, . . . are disposed at the interval of the vertical welded parts c along the guide rail 4 in this case, the sensor 10 will make contact with any of the limit switches 9 to thus cause the electric chain block 8 to be stopped. Accordingly, the X-ray generator 6 is accurately positioned at the respective vertical welded parts c.

The drive means 13 of the penetrameter support 12 is energized by the operation on the operation panel 24, thereby starting the drive means 13. Thus, the penetrameter 11 is urged on the surface of the wall 2 to be inspected, a film 14 is then bonded to the opposite side of the wall 2 to be inspected, and then the X-ray photographing is taken for the welded part c.

The film 14 is bonded onto the wall 2 to be inspected by opening the door 24b from the interior of the gondola 24, and the X-ray photographing is conducted on the operation panel (32) within the gondola 24 by closing the door 24b. Since at least the front surface of the gondola 24 is formed of lead stationary frame 24a and the openable door 24b for transmitting no X-ray, the worker may not be contaminated by the X-ray irradiated upon photographing.

Then, the X-ray generator 6 and the gondola 24 are sequentially lowered or raised, and the respective vertical welded parts c, . . . can be thus photographed with the X-ray.

After the respective vertical welded parts c, . . . are thus photographed in a unit vertical row, the pushing means 16 of the supporting leg 5 is operated, and the wheel 17 is thus moved and pushed forwardly and is pushed onto the wall 2 to be inspected. Then, the magnets 15, 15 are isolated from the surface of the wall 2 to be inspected. Accordingly, the motor 28 is then started, and the body 1 is laterally moved along the upper edge 2a of the wall 2 to be inspected via the horizontally moving wheels 3, 3, and is stopped on the next unit vertical welded part row, and the same operations as described above will be sequentially conducted and the respective vertical welded parts c will be photographed with the X-ray.

It should be noted that, although the above embodiment is directed to the limit switches 9 used as the stopping means of the X-ray generator 6, the control of the energizing time of the electric chain block 8 may be utilized for elevationally driving the X-ray generator 6.

It is to be observed therefore from the foregoing description that the X-ray photographic inspecting device of this invention for inspecting a welded part on a wall of a metal tank or the like comprises the body 1 which is laterally movable with the upper edge 2a of the wall 2 to be inspected as a guide and hung on the upper edge 2a of the wall 2. It is operated by a worker or operator 26 on the gondola 24 elevationally driven in synchronism with the X-ray generator 6, which is on the gondola 24 by an operation panel 32. The body or housing 1 is fixed to the wall 2 by magnets 15 of the supporting leg 5 and the pushing means 16 thereof or releasing the fixture of the body 1, the transmitter 11 is urged onto the wall 2 to be inspected. A film 14 is bonded on the opposite side surface of the wall 2. The X-ray photographing as well as all operations are done by one worker 26 and the X-ray generator 6 can be accurately and rapidly positioned on the welded part to be photographed at every photographic frame of the X-ray generator 6 by the use of the limit switches 9, . . . at the predetermined interval of the welded parts in a vertical row along the guide rail 4 of the X-ray generator 6 or controlling the energizing time of the electric chain block 8 to correspond to the interval of the vertical welded parts c with respect to the elevationally moving speed, it can save labor the control of the X-ray photographic inspecting device, can largely improve the working efficiency with safety as its advantages.

What is claimed is:

1. A weld flaw-detection apparatus using X-ray photography, where the X-ray apparatus is to be positioned on one side of a high wall, and operated by a technician who will enable the apparatus to send an X-ray beam through the wall to a film positioned on the other side of the wall, said apparatus comprising in combination:

(a) a movable housing (1) with an upper and lower end, a positioning section at said upper end for positioning at the upper edge of a wall having welds therealong which are to be examined for flaws, including support means for supporting said housing (1);

(b) a vertical guide rail (4) so disposed as to extend down from said housing (1) on one side of said wall, movable and adjustable limit switches (9) for positioning along said guide rail (4) at predetermined positions;

(c) a transmitter support (13) including drive means, elevationally and movably hung on said guide rail (4), an X-ray generator (6) generating penetrating X-rays, and an X-ray transmitter (11), coupled to said generator, on said support (13), said X-ray transmitter being disposed for beaming penetrating X-rays through the wall at said perdetermined positions where welds are located so as to determine if there are flaws in said welds;

(d) a lead-shielded movable gondola (24) for holding an operator including cable means (25) connected to the housing (1), said gondola being arranged to be disposed on the side of the wall opposite said transmitter (11), a door on said gondola openable towards the wall to place a film material thereon to receive any transmitted X-rays from said X-ray transmitter; and, (e) a supporting leg (5) of U-shape configuration at the lower end of said housing, said supporting leg having leg frame means (5a) with inner ends which are to be placed opposite said wall, a pair of magnets (15) at said inner ends disposed to engage the wall to be inspected, a guide rail (4) across said leg frame means (5a), a first pivot (20) on said guide rail (4), a cylinder (21) having a pivoted end, pivoted to said first pivot (20) and an output piston shaft (21a), telescoped into said cylinder (21), said output shaft having an output end, a second pivot (19) on said leg frame means (5a), an arm (18) with one end pivoted to said second pivot (19) and the other end being connected to said output end, a wheel (17), journaled on said arm (18) between said leg frame means (5a) so that when said output shaft (21a) extends out of the cylinder (21) it pushes said wheel against the wall to be examined, separating the magnets (15) from contact with the wall.

* * * * *